United States Patent

Baroni et al.

[11] Patent Number: 5,488,151
[45] Date of Patent: Jan. 30, 1996

[54] {(7S)-7-[(2R)-2-(3-CHLOROPHENYL)-2-HYDROXYETHYLAMINO)-2-HYDROXYETHYLAMINO]-5,6,7,8-TETRAHYDRONAPHTHALEN-2-YLOXY} ACETIC ACID AND ITS PHARMACEUTICALLY ACCEPTABLE SALTS

[75] Inventors: Marco Baroni, Vanzago; Roberto Cecchi, Lodi; Tiziano Croci, Milan, all of Italy

[73] Assignee: Sanofi, Paris, France

[21] Appl. No.: 250,830

[22] Filed: May 31, 1994

[30] Foreign Application Priority Data

May 28, 1993 [EP] European Pat. Off. ............ 93401375

[51] Int. Cl.⁶ .................................................. C07C 229/40
[52] U.S. Cl. ......................................... 562/452; 560/45
[58] Field of Search ..................... 562/452; 560/45; 514/567; 424/1.81, 1.85

[56]  References Cited

U.S. PATENT DOCUMENTS

| | | | |
|---|---|---|---|
| 4,707,497 | 11/1987 | Cecchi et al. ........................... | 514/647 |
| 4,927,955 | 5/1990 | Boigegrain et al. ..................... | 560/45 |
| 5,002,946 | 3/1991 | Manara et al. .......................... | 514/230.8 |
| 5,130,339 | 7/1992 | Cecchi et al. ........................... | 514/653 |
| 5,198,586 | 3/1993 | Boigegrain et al. ..................... | 564/356 |
| 5,235,103 | 8/1993 | Boigegrain et al. ..................... | 564/170 |
| 5,312,961 | 5/1994 | Guzzi et al. ............................ | 560/45 |

OTHER PUBLICATIONS

Wolff (Ed.), *Burger's Medicinal Chemistry*, 4th Edition, 1980 (New York: John Wiley & Sons).

*Primary Examiner*—José G. Dees
*Assistant Examiner*—Barbara S. Frazier
*Attorney, Agent, or Firm*—Bacon & Thomas

[57]  ABSTRACT

The present invention relates to the novel compound {(7S)-7-[(2R)-2-(3-chlorophenyl)-2-hydroxyethylamino]-5,6,7,8-tetrahydronaphthalen-2-yloxy}acetic acid of formula (I):

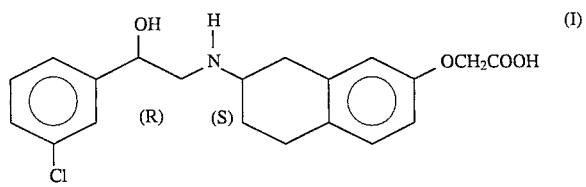

and its pharmaceutically acceptable salts, which act as $\beta_3$-adrenergic agonists, and to the pharmaceutical compositions and laboratory reagents in which it is present.

11 Claims, No Drawings

{ (7S)-7-[ (2R)-2-(3-CHLOROPHENYL)-2-HYDROXYETHYLAMINO)-2-HYDROXYETHYLAMINO]-5,6,7,8-TETRAHYDRONAPHTHALEN-2-YLOXY} ACETIC ACID AND ITS PHARMACEUTICALLY ACCEPTABLE SALTS

The present invention relates to a novel phenylethanolamine derivative and its pharmaceutically acceptable salts, which act as $\beta_3$-adrenergic agonists, and to the pharmaceutical compositions in which it is present.

European patents 211 721, 255 415 and U.S. Pat. No. 4,927,955 describe phenylethanolamines having lipolytic and spasmolytic activity. These two activities are the result of a particular mechanism of action which has only been demonstrated very recently and which involves the $\beta_3$-adrenergic receptors.

Among the compounds described in the above-mentioned patents, ethyl {(7S)-7-[(2R)-2-(3-chlorophenyl)-2-hydroxyethylamino]-5,6,7,8-tetrahydronaphthalen-2-yloxy)acetate has proved very effective in stimulating the $\beta_3$-adrenergic receptors and has been selected for human clinical trials.

It has now been found that this compound is subjected to biomodifications by the metabolic enzymes, especially the hydrolases, and is transformed to a metabolite, namely its corresponding acid, which is also active but is even more selective than the starting material.

It is known that, in general, the administration of the metabolite in place of its pro-drug analog is an advantageous therapy because the metabolite is no longer subject to biochemical transformations in the organism; on the contrary, it is already ready to exert its effect at the site of action.

Furthermore, the metabolic pathway for which the pro-drug compound is destined is not unique and the administered drug can be metabolically transformed to different derivatives which are less effective in some cases and inactive in others.

In the present case, it has been found, surprisingly, that the principal metabolite of the above compound is the corresponding acid and that this is more selective than the pro-drug compound, so the desired therapeutic effect is obtained more selectively, the side-effects becoming even weaker.

Moreover, the greater selectivity makes the above compound particularly indicated for the labeling of the $\beta_3$-adrenergic receptors.

The present invention relates, by way of a novel compound, to {(7S)-7-[(2R)-2-( 3-chlorophenyl)-2-hydroxyethylamino]- 5,6,7,8-tetrahydronaphthalen-2-yloxy}acetic acid of formula (I), which acts as a $\beta_3$-adrenergic agonist.

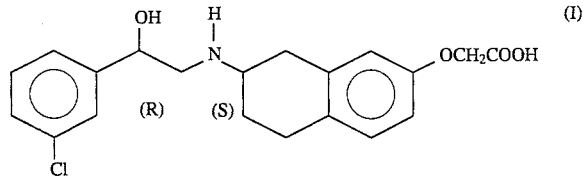

{(7S)-7-[(2R)-2-(3-Chlorophenyl)- 2-hydroxyethylamino]- 5,6,7,8-tetrahydronaphthalen-2-yloxy}acetic acid (I) has two asymmetric carbon atoms of fixed stereochemistry. Mixtures of isomers containing said compound also form part of the present invention.

The present invention further relates to the pharmaceutically acceptable salts of the compound of formula (I).

The amphoteric character of the compound of formula (I) enables pharmaceutically acceptable salts to be prepared either with pharmaceutically acceptable acids or with pharmaceutically acceptable bases.

Examples of salts with pharmaceutically acceptable bases are those with alkali metals or alkaline earth metals such as sodium, potassium, calcium and magnesium, and those with organic bases such as amines, basic amino acids (lysine, arginine, histidine), trometamol, etc.

Examples of salts with pharmaceutically acceptable acids are those with mineral acids, such as the hydrochloride, hydrobromide, borate, phosphate, sulfate, hydrogensulfate and hydrogenphosphate, and those with organic acids, such as the citrate, benzoate, ascorbate, methylsulfate, naphthalene-2-sulfonate, picrate, fumarate, maleate, malonate, oxalate, succinate, acetate, tartrate, mesylate, tosylate, $\alpha$-ketoglutarate, $\alpha$-glycerophosphate, glucose-1-phosphate, etc.

Salification is effected by treatment with the chosen acid or base in an organic solvent by the methods well known to those skilled in the art.

The compound of formula (I) is easily prepared by hydrolysis of the corresponding ethyl ester, whose method of synthesis is described in European patent 303 546.

The present invention further relates to the use of the acid of formula (I), or one of its pharmaceutically acceptable salts, for the preparation of drugs intended for the treatment and/or prophylaxis of pathological conditions which can be improved by means of an agonistic action mediated by the receptors of the $\beta_3$-adrenergic type, examples being obesity, eye complaints and gastrointestinal disorders due to contraction of the smooth muscle, especially in the irritable colon.

The acid of formula (I) and its pharmaceutically acceptable salts can also be used for the preparation of drugs for combating depression, anxiodepressive disorders and certain consequences of stress, such as anxiety.

According to another feature, the present invention relates to the compound of formula (I) above or one of its salts, labeled on one of its atoms. More particularly, the invention relates to the compound of formula (I) in which one of the hydrogen atoms is replaced with a tritium atom.

The present invention further relates to a laboratory reagent in which the compound of formula (I) or one of its salts, either as such or labeled, is present as the active product.

The present invention will now be illustrated by the Example below:

EXAMPLE 1

{(7S)-7-[(2R)-2-(3-Chlorophenyl)-2-hydroxyethylamino]-5,6,7,8-tetrahydronaphthalen-2-yloxy{acetic acid 4.4 g (0.108 mol) of ethyl ((7S)-7-[(2R)- 2-(3-chlorophenyl)- 2-hydroxyethylamino]-5,6,7,8-tetrahydronaphthalen-2-yloxy}acetate are dissolved in 15 ml of ethyl alcohol, and 10.5 ml of 1 N NaOH are added. The mixture is stirred for 30 min. at room temperature and 30 min. at 40°–50° C. It is evaporated under reduced pressure and the residue is dissolved in 50 ml of water. The solution is washed with ethyl ether, the two phases are separated and 10.5 ml of 1 N hydrochloric acid are added to the aqueous phase. The precipitate obtained is triturated, filtered off and washed with water to give 2.5 g of the title product. M.p. 215° C. dec. $[\alpha]_{20}=-98.4°$ (0.5% MeOH/1 N HCl).

The compound of formula (I) and its pharmaceutically acceptable salts are potent and selective $\beta_3$-adrenergic agonists; their activity was evaluated by means of either in vitro or in vivo tests.

For evaluation of the selective $\beta_3$-adrenergic agonism, the compound of formula (I) was subjected to the tests described in European patent 436 435.

The compound of formula (I) was found to be very active in the in vitro test on rat proximal colon, but completely inactive in the tests on rat uterus and guinea-pig right atrium.

Also, in vivo tests on intestinal motivity were carried out on the anesthetized rat by the method described in European patent 255 415; the compound of formula (I) was found to be very effective in this test as well.

The agonistic activity of the compound of formula (I) and that of its pharmaceutically acceptable salts towards the $\beta_3$-adrenergic receptors manifests itself as a lipolysis-stimulating and intestinal motivity-modulating effect and as an antidepressant and anxiolytic effect.

Also by virtue of their low toxicity, the compound of formula (I) and its pharmaceutically acceptable salts can therefore certainly be used in therapy in the treatment and/or prophylaxis of gastrointestinal disorders in mammals, such as those due to contractions of the smooth muscle, more particularly the irritable colon, and the spasms which accompany peptic ulcer.

The compound of formula (I) can also be used in cases of obesity by virtue of its lipolysis-stimulating effect.

The acid of formula (I) and its pharmaceutically acceptable salts can also be used in depressive and anxio-depressive states and in anxiety caused by stress.

It is also possible to envisage using the compound of formula (I) in the treatment of eye complaints, especially for the control of intraocular pressure and the treatment of ocular hypertension and glaucoma.

The present invention further relates to the pharmaceutical compositions in which the compound of formula (I) and its pharmaceutically acceptable salts are present as the active principle.

For its use in therapeutics, the product of formula (I), either pure or in association with any other pharmaceutically compatible substance, can be used in appropriate pharmaceutical forms intended for oral, parenteral, sublingual, rectal, transdermal and topical administration.

For oral administration, it is possible for example to use tablets, coated tablets, granules or liquid compositions such as syrups, elixirs, emulsions or solutions.

It is possible to use aqueous or non-aqueous injectable sterile compositions for parenteral administration, suppositories for rectal administration and patches for transdermal administration; if appropriate, it is possible to prepare delayed-release forms or forms in which the active principle of formula (I) is included in liposomes or in cyclodextrins.

These pharmaceutical forms are prepared by the conventional methods, the active principle of formula (I) being mixed with the excipients and additives normally employed in the art of pharmaceutics, such as starch, lactose, talc, magnesium stearate, sucrose, paraffin oil, wetting products, flavorings, stabilizers, etc.

The pharmaceutical compositions according to the invention advantageously contain, as the active principle, from 0.01 to 500 mg of the compound of formula (I) or one of its pharmaceutically acceptable salts.

The appropriate dosage in the therapeutic use of these compositions has to be evaluated in each individual case by considering the characteristics of the subjects to be treated, namely the age, the body weight and the severity of the complaints to be treated. In general, the therapeutic use of the compound of formula (I) provides for the administration of a dosage of between 0.01 and 100 mg/kg per day, preferably between 0.1 and 50 mg, optionally subdivided into doses to be administered several times a day, the preferred posology being one to three times a day.

If the compound of formula (I) is employed in the treatment of eye complaints, pharmaceutical compositions for topical administration to the eye are used, examples being suspensions, solutions, ointments and gels, which are prepared by the known methods in a manner appropriate to this specific application.

The ophthalmic formulations can contain from 0.00001 to 1% by weight of the compound of formula (I), more particularly from 0.0001 to 0.2%.

The suggested posology for this topical therapy is between 10 ng and 1 mg of active principle per day, preferably subdivided into doses to be administered several times a day, the preferred posology being one to three times a day.

What is claimed is:

1. {(7S)-7-[(2R)-2-(3-Chlorophenyl )-2-hydroxyethylamino]- 5,6,7,8-tetrahydronaphthalen-2-yloxy}acetic acid of formula (I):

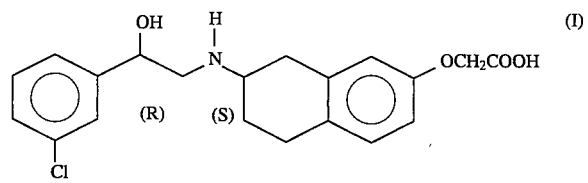

and its pharmaceutically acceptable salts.

2. The sodium salt of the compound of claim 1.

3. A pharmaceutical composition in which the compound of claim 1 is present as the active principle.

4. A pharmaceutical composition of claim 3 containing from 0.01 to 500 mg of active principle.

5. A laboratory reagent in which a compound according to claim 1, either as such or labeled by replacing one of its hydrogen atoms by a tritium atom, is present as the active product.

6. A method for the treatment of pathological conditions which can be improved by means of an agonistic action mediated by the receptors of the $\beta_3$-adrenergic type which comprises administering to a patient in need thereof an effective amount of a composition containing the compound of claim 1 or its pharmaceutically acceptable salts.

7. The method of claim 6 for the treatment of gastrointestinal disorders due to contraction of the smooth muscle.

8. The method of claim 7 for the treatment of irritable colon.

9. The method of claim 6 for the treatment of obesity.

10. The method of claim 6 for the treatment of depressive and anxio-depressive states and anxiety caused by stress.

11. The method of claim 6 for the treatment of eye complaints.

* * * * *